(12) United States Patent
Akatsu et al.

(10) Patent No.: US 11,160,508 B2
(45) Date of Patent: Nov. 2, 2021

(54) BIOLOGICAL INFORMATION MONITORING SYSTEM

(71) Applicant: Minebea Mitsumi Inc., Nagano (JP)

(72) Inventors: Hiroyuki Akatsu, Minato-ku (JP); Norihito Iida, Sagamihara (JP)

(73) Assignee: MINEBEA MITSUMI INC., Nagano (JP)

( * ) Notice: Subject to any disclaimer, the term of this patent is extended or adjusted under 35 U.S.C. 154(b) by 0 days.

(21) Appl. No.: 16/194,832

(22) Filed: Nov. 19, 2018

(65) Prior Publication Data

US 2019/0150844 A1    May 23, 2019

Related U.S. Application Data

(63) Continuation of application No. PCT/JP2017/018543, filed on May 17, 2017.

(30) Foreign Application Priority Data

May 20, 2016    (JP) ............................... JP2016-101355

(51) Int. Cl.
*A61B 5/00* (2006.01)
*A61B 5/113* (2006.01)
(Continued)

(52) U.S. Cl.
CPC .............. *A61B 5/6892* (2013.01); *A61B 5/00* (2013.01); *A61B 5/0205* (2013.01);
(Continued)

(58) Field of Classification Search
USPC ....................................................... 600/484
See application file for complete search history.

(56) References Cited

U.S. PATENT DOCUMENTS 3,890,958 A * 6/1975 Fister ................... A61B 5/1102
600/527
4,657,025 A    4/1987 Orlando
(Continued)

FOREIGN PATENT DOCUMENTS

CN    101632579 A    1/2010
EP    2 148 179 A1    1/2010
(Continued)

OTHER PUBLICATIONS

Decision to Grant a Patent dated Nov. 22, 2017 for corresponding Japanese Application No. 2016-101355 and English translation.
(Continued)

*Primary Examiner* — David J. McCrosky
*Assistant Examiner* — Chanel J Jhin
(74) *Attorney, Agent, or Firm* — Pearne & Gordon LLP

(57) ABSTRACT

There is provided a biological information monitoring system for monitoring a biological information on a subject on a bed. The system includes a plurality of load detectors which are to be placed in the bed or under legs of the bed, and which are configured to detect a load of the subject; a load separation unit configured to separate a load component which oscillates according to a heartbeat of the subject, from the load of the subject; and a center of gravity position calculation unit configured to obtain a position of a center of gravity of the subject based on the load component which oscillates according to the heartbeat of the subject.

7 Claims, 5 Drawing Sheets

(51) Int. Cl.
*G08B 21/06* (2006.01)
*A61B 5/0245* (2006.01)
*A61B 5/11* (2006.01)
*A61G 7/05* (2006.01)
*G08B 21/22* (2006.01)
*A61B 5/08* (2006.01)
*A61B 5/0205* (2006.01)

(52) U.S. Cl.
CPC .............. *A61B 5/0245* (2013.01); *A61B 5/08* (2013.01); *A61B 5/11* (2013.01); *A61B 5/1102* (2013.01); *A61B 5/113* (2013.01); *A61G 7/05* (2013.01); *G08B 21/06* (2013.01); *G08B 21/22* (2013.01); *A61B 2562/0252* (2013.01); *A61B 2562/046* (2013.01)

(56) References Cited

U.S. PATENT DOCUMENTS

| | | | |
|---|---|---|---|
| 4,738,264 A | | 4/1988 | Orlando |
| 5,291,013 A | * | 3/1994 | Nafarrate ............... A61B 5/113 128/925 |
| 2005/0096559 A1 | * | 5/2005 | Yanai ..................... A61B 5/113 600/534 |
| 2007/0149883 A1 | * | 6/2007 | Yesha .................. A61B 5/1102 600/485 |
| 2007/0191742 A1 | * | 8/2007 | Park .......................... A61B 5/11 600/587 |
| 2008/0005838 A1 | * | 1/2008 | Wan Fong ......... A61B 5/02444 5/600 |
| 2012/0116187 A1 | | 5/2012 | Hayes et al. |
| 2014/0371635 A1 | * | 12/2014 | Shinar ................. A61B 5/6891 600/595 |
| 2015/0073283 A1 | | 3/2015 | Van Vugt et al. |
| 2015/0351694 A1 | * | 12/2015 | Shimizu ............. A61B 5/02444 600/508 |
| 2016/0120716 A1 | * | 5/2016 | Ribble ................. A61B 5/6892 5/616 |
| 2018/0206793 A1 | | 7/2018 | Akatsu et al. |
| 2018/0353358 A1 | * | 12/2018 | Lingegard ................ A61G 7/05 |

FOREIGN PATENT DOCUMENTS

| | | |
|---|---|---|
| JP | 61-24010 B2 | 6/1986 |
| JP | 4002905 B2 | 11/2007 |
| JP | 2010-032241 A | 2/2010 |
| JP | 4829020 B2 | 11/2011 |
| JP | 4883380 B2 | 2/2012 |
| JP | 2012-040441 A | 3/2012 |
| JP | 2014-061174 A | 4/2014 |
| JP | 2014-180432 A | 9/2014 |
| JP | 2017-064350 A | 4/2017 |
| WO | 2009/127405 A1 | 10/2009 |
| WO | 2011/009085 A2 | 1/2011 |

OTHER PUBLICATIONS

International Search Report for International Application No. PCT/JP2017/018543 dated Aug. 1, 2017.
Written Opinion for International Application No. PCT/JP2017/018543 dated Aug. 1, 2017 and English translation.
Chinese Office Action dated May 23, 2019 for corresponding Chinese Application No. 201780042545.0 and English translation.
Extended European Search Report dated Nov. 27, 2019 for corresponding European Application No. 17799434.0.
Chinese Office Action dated Nov. 14, 2019 for corresponding Chinese Application No. 201780042545.0 and English translation.
Chinese Office Action dated Apr. 9, 2020 for corresponding Chinese Application No. 201780042545.0 and English translation.
Chinese Office Action dated Aug. 31, 2020 for corresponding Chinese Application No. 201780042545.0 and English translation.

* cited by examiner

BIOLOGICAL INFORMATION MONITORING SYSTEM

CROSS-REFERENCE TO RELATED APPLICATIONS

This application is a Continuation Application of International Application No. PCT/JP2017/018543 claiming the conventional priority of Japanese patent Application No. 2016-101355 filed on May 20, 2016, and titled "BIOLOGICAL INFORMATION MONITORING SYSTEM". The disclosures of Japanese patent Application No. 2016-101355, and International Application No. PCT/JP2017/018543 are incorporated herein by reference in their entirety.

BACKGROUND

The present disclosure relates to a biological information monitoring system for monitoring biological information of a subject (a human subject).

Biological information of a subject is one of the important pieces of information for knowing the physical condition (body condition) of a patient or a care receiver in the sites of the medical treatment and the care. For example, the respiratory condition (respiratory state) of the subject is grasped and can be utilized to grasp the symptoms of, for example, the sleep apnea syndrome (SAS) and the snore; and to improve (alleviate) the symptoms.

It has been suggested that load sensors are arranged under legs of a bed to measure the respiratory condition of a subject on the basis of measured values of the load sensors (Japanese Patent No. 4883380). Further, it has been also suggested that load detectors are arranged under legs of a bed to acquire (obtain) the movement of the center of gravity of a subject living body on the bed so that the respiratory movement (breathing movement) and the heartbeat movement of the subject living body are acquired on the basis of the movement of the center of gravity (Japanese Publication of Examined Patent Application No. 61-24010).

Citation List

SUMMARY

In the sites of the medical treatment, it is desired to accurately grasp the center of gravity position of a subject on a bed; however, the inventions described in Japanese Patent No. 4883380 and Japanese Publication of Examined Patent Application No. 61-24010 fail to meet such on-site demands.

An object of the present disclosure is to provide a biological information monitoring system which enables to grasp a center of gravity position of a subject on a bed accurately.

According to a first aspect of the present disclosure, there is provided a biological information monitoring system for monitoring a biological information on a subject on a bed, the system including: a plurality of load detectors which are to be placed in the bed or under legs of the bed, and which are configured to detect a load of the subject; a load separation unit configured to separate a load component which oscillates according to a heartbeat of the subject, from the load of the subject; and a center of gravity position calculation unit configured to obtain a position of a center of gravity of the subject based on the load component which oscillates according to the heartbeat of the subject.

EMBODIMENTS

First Embodiment

A first embodiment of the present disclosure will be explained with reference to FIGS. 1 to 7.

Figure 1:
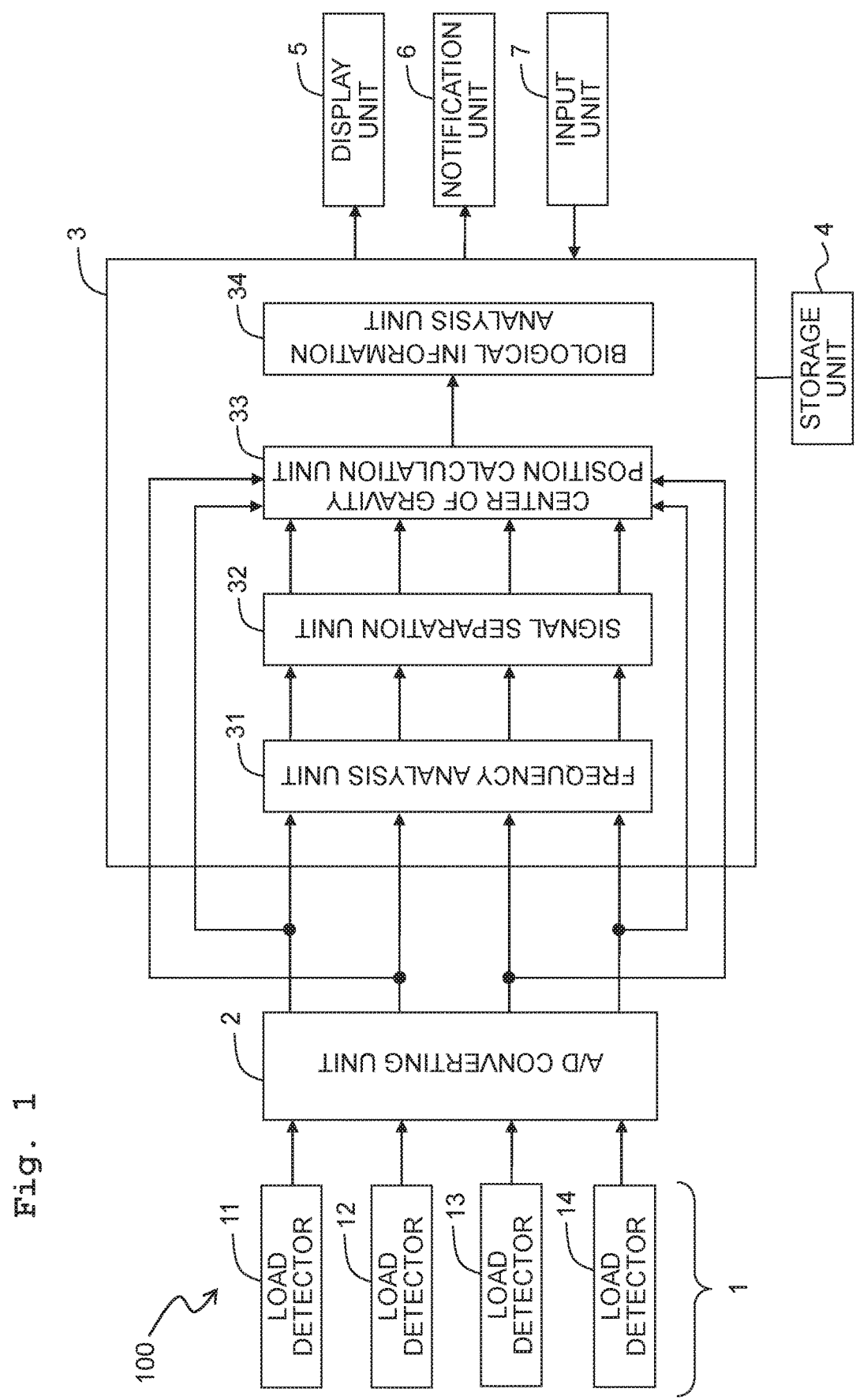
FIG. 1 is a block diagram depicting a configuration of a biological information monitoring system according to an embodiment of the present disclosure.

As depicted in FIG. 1, a biological information monitoring system (respiratory waveform drawing system, respiratory information acquiring system) 100 of this embodiment is provided to perform the observation and the measurement in order to grasp the biological state or condition of a subject (a human subject, that is, a person being monitored) on a bed. The biological information monitoring system 100 principally includes a load detecting unit 1, a control unit (a controller) 3, a storage unit (a storage) 4, and a display unit (a display) 5. The load detecting unit 1 and the control unit 3 are connected via an A/D converting unit 2. A notification unit 6 and an input unit 7 are further connected to the control unit 3.

The load detecting unit 1 is provided with four load detectors 11, 12, 13, 14. Each of the load detectors 11, 12, 13, 14 is a load detector which detects the load by using, for example, a beam-type load cell. Such a load detector is described, for example, in Japanese Patent No. 4829020 and Japanese Patent No. 4002905. Each of the load detectors 11, 12, 13, 14 is connected to the A/D converting unit 2 by means of wiring.

Figure 2:
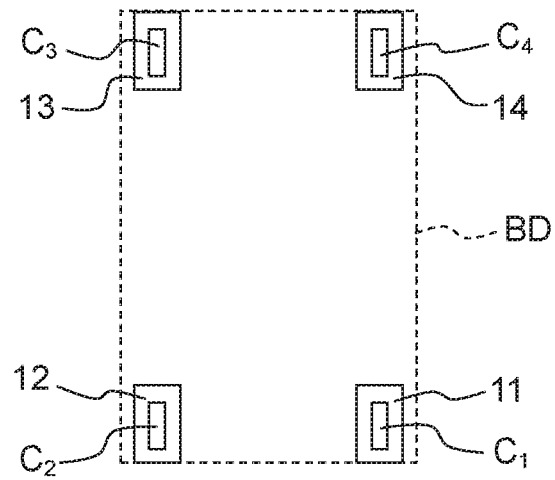
FIG. 2 is an illustrative view depicting an arrangement of load detectors with respect to a bed.

The four load detectors 11, 12, 13, 14 of the load detecting unit 1 are arranged under the legs of a bed to be used by the subject. Specifically, as depicted in FIG. 2, the load detectors 11, 12, 13, 14 are arranged respectively on the undersides of casters $C_1$, $C_2$, $C_3$, $C_4$ attached to lower end portions of the legs disposed at the four corners of the bed BD.

The A/D converting unit 2 is provided with an A/D converter which converts the analog signal fed from the load detecting unit 1 into the digital signal. The A/D converting unit 2 is connected to each of the load detecting unit 1 and the control unit 3 by means of wiring.

The control unit 3 is an exclusive or general-purpose computer. A frequency analysis unit (a frequency analyzer) 31, a signal separation unit (a signal separator) (a load separation unit, or a load separator) 32, a center of gravity position calculation unit (a center of gravity position calculator) 33, and a biological information analysis unit (a biological information analyzer) (presence-on-bed determination unit) 34 are constructed therein.

The storage unit 4 is a storage device which stores the data used for the biological information monitoring system 100. For example, it is possible to use a hard disk (magnetic disk) therefore. The display unit 5 is a monitor, such as a liquid crystal monitor, for displaying the information outputted from the control unit 3 for a user of the biological information monitoring system 100.

The notification unit 6 is provided with a device for visually or auditorily performing predetermined notification on the basis of the information fed from the control unit 3, for example, a speaker. The input unit 7 is an interface for performing predetermined input for the control unit 3, and may be a keyboard and a mouse.

It is possible to detect and monitor various biological information, such as the respiratory condition of the subject on the bed, by using the biological information monitoring system 100 described above. The acquisition and the monitoring of various biological information are performed on the basis of the variation of the center of gravity position of the subject on the bed.

Figure 3:
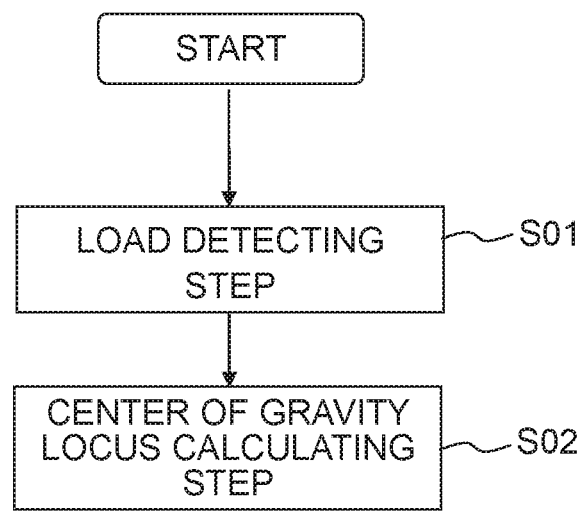
FIG. 3 is a flow chart depicting a center of gravity locus (trajectory path) calculation method according to the embodiment of the present disclosure.

An explanation will be given about the operation for calculating the center of gravity position of the subject on the bed, by using the biological information monitoring system 100. As depicted in FIG. 3, the calculation of the center of gravity position of the subject, which is based on the use of the biological information monitoring system 100, includes a load detecting step (S01) of detecting the load of the subject and a center of gravity locus calculating step (S02) of calculating the temporal variation of the position of the center of gravity of the subject (center of gravity locus) on the basis of the detected load.

Figure 4:
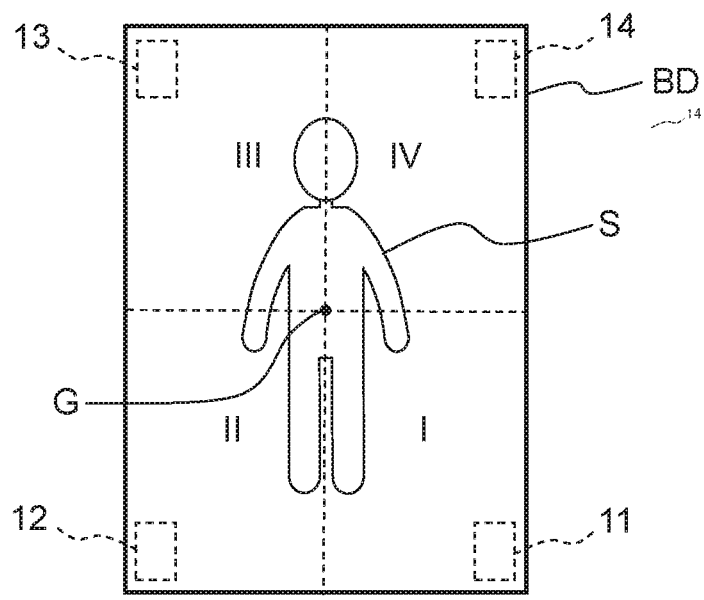
FIG. 4 is an illustrative view depicting an arrangement of four load detection areas defined on the upper surface of the bed.

In the load detecting step S01, the load of the subject S on the bed BD is detected, by using the load detectors 11, 12, 13, 14. As the load detectors 11, 12, 13, 14 are arranged respectively on the undersides of the casters $C_1$, $C_2$, $C_3$, $C_4$ as described above, the load, which is applied to the upper surface of the bed BD, is detected in a dispersed manner by the four load detectors 11, 12, 13, 14. Specifically, as depicted in FIG. 4, the rectangular upper surface of the bed BD is longitudinally divided into two and laterally divided into two, and thus the upper surface is equally divided into four rectangular areas I to IV.

Accordingly, the load, which is applied to the area I positioned with the left lower half of the body of the subject S lying on his/her back (face up) at the central portion of the bed BD, is principally detected by the load detector 11, and the load, which is applied to the area II positioned with the right lower half of the body of the subject S in the same state, is principally detected by the load detector 12. Similarly, the load, which is applied to the area III positioned with the right upper half of the body of the subject S lying on his/her back at the central portion of the bed BD, is principally detected by the load detector 13, and the load, which is applied to the area IV positioned with the left upper half of the body of the subject S in the same state, is principally detected by the load detector 14. Note that when the subject S does not exist on the bed BD, the total of the outputs from the load detectors 11, 12, 13, 14 represents the weight of the bed itself. When the subject S exists on the bed BD, the total of the outputs from the load detectors 11, 12, 13, 14 represents the weight of the bed and the body weight of the subject S. Therefore, it is possible to measure the body weight of the subject S when the subject S exists on the bed, by previously storing the weight of the bed itself in the storage unit 4. Note that when the weight of the bed is not uniform among the four areas, the difference therebetween is stored beforehand as the bed weight corresponding to each of the load detectors. Further, it is desirable that the situation in which any weight other than that of the subject S is brought about during the actual measurement, for example, the placement of any bedding, any baggage or the like is reflected to the weight of the bed.

Each of the load detectors 11, 12, 13, 14 detects the load (load change), and the load (load change) is outputted as the analog signal to the A/D converting unit 2. The A/D converting unit 2 converts the analog signal into the digital signal (hereinafter referred to as "load signal") while using the sampling period of, for example, 5 milliseconds, and the load signal is outputted to the center of gravity position calculation unit 33 not through the frequency analysis unit 31 and the signal separation unit 32.

Figure 5:
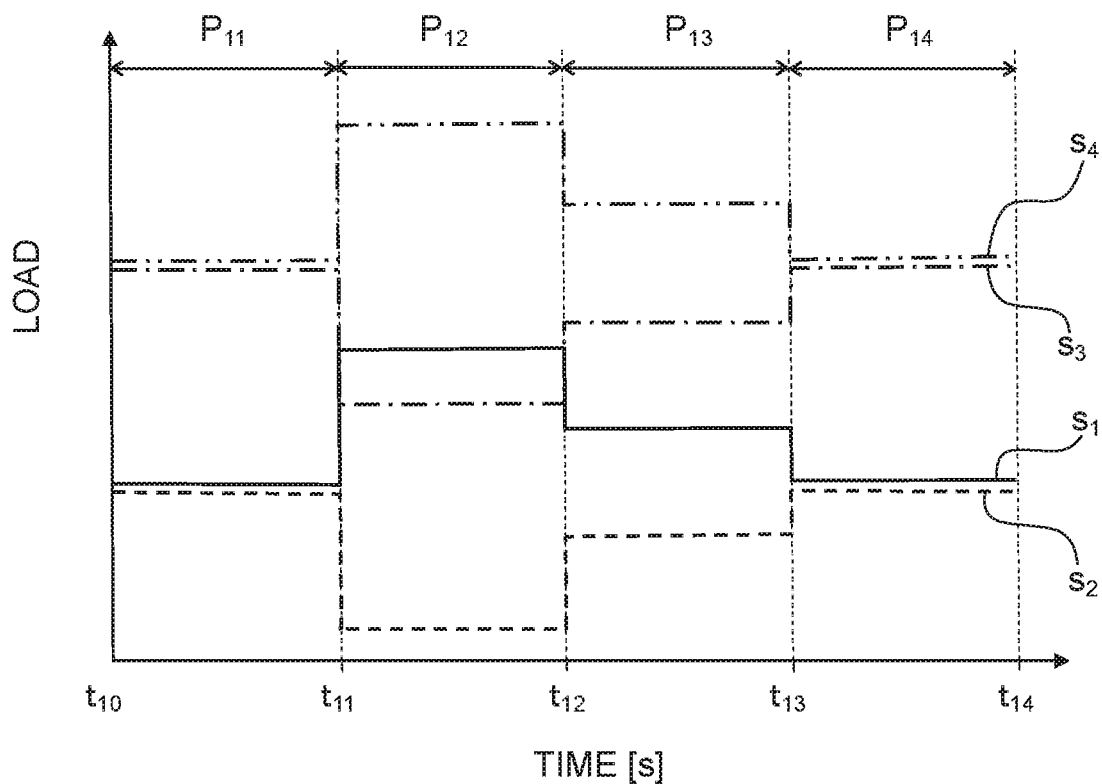
FIG. 5 depicts exemplary load signals fed from the load detectors.

Exemplary load signals are depicted in FIG. 5. FIG. 5 depicts the load signals $s_1$ (solid line), $s_2$ (broken line), $s_3$ (alternate long and short dash line), and $s_4$ (alternate long and two short dashes line) fed from the load detectors 11, 12, 13, 14 as outputted during the period ranging from the time $t_{10}$ to the time $t_{14}$. The following fact has been observed. That is, the subject S lay on his/her back at the central portion of the bed BD as depicted in FIG. 4 during the period ranging from the time $t_{10}$ to the time $t_{11}$ (period $F_{11}$). The subject S moved to the side of the areas I, IV of the bed BD during the period ranging from the time $t_{11}$ to the time $t_{12}$ (period $P_{12}$). The subject S moved to some extent to the central side of the bed BD during the period ranging from the time $t_{12}$ to the time $t_{13}$ (period $P_{13}$) as compared with the period $P_{12}$. The subject S lay on his/her back at the central portion of the bed BD during the period ranging from the time $t_{13}$ to the time $t_{14}$ (period $P_{14}$).

During the period $P_{11}$, the subject S lay on his/her back at the central portion of the bed BD as depicted in FIG. 4. Therefore, during the period $P_{11}$, the signals $s_3$, $s_4$, which are fed from the load detectors 13, 14 arranged on the head side of the subject S, are approximately equal to one another, and the signals $s_1$, $s_2$, which are fed from the load detectors 11, 12 arranged on the foot side of the subject S, are approximately equal to one another.

During the period $P_{12}$, the subject S moved to the side of the areas I, IV of the bed BD. Therefore, during the period $P_{12}$, the signals $s_1$, $s_4$, which are fed from the load detectors 11, 14 arranged in the areas I, IV, exhibit the large load values as compared with the period $P_{11}$, and the signals $s_2$, $s_3$, which are fed from the load detectors 12, 13 arranged in the areas II, III, exhibit the small load values as compared with the period $P_{11}$.

During the period $P_{13}$, the subject S moved to some extent to the central side of the bed BD as compared with the period $P_{12}$. Therefore, during the period $P_{13}$, the signals $s_1$, $s_4$, which are fed from the load detectors 11, 14 arranged in the areas I, IV, exhibit the small load values as compared with the period $P_{12}$, and the signals $s_2$, $s_3$, which are fed from the load detectors 12, 13 arranged in the areas II, III, exhibit the large load values as compared with the period $P_{12}$.

During the period $P_{14}$, the subject S lay on his/her back at the central portion of the bed BD in the same manner as the period $P_{11}$. Therefore, during the period $P_{14}$, the signals $s_1$ to $s_4$, which are provided during the period $P_{14}$, are the same as the signals $s_1$ to $s_4$ provided during the period $P_{11}$.

Figure 6:
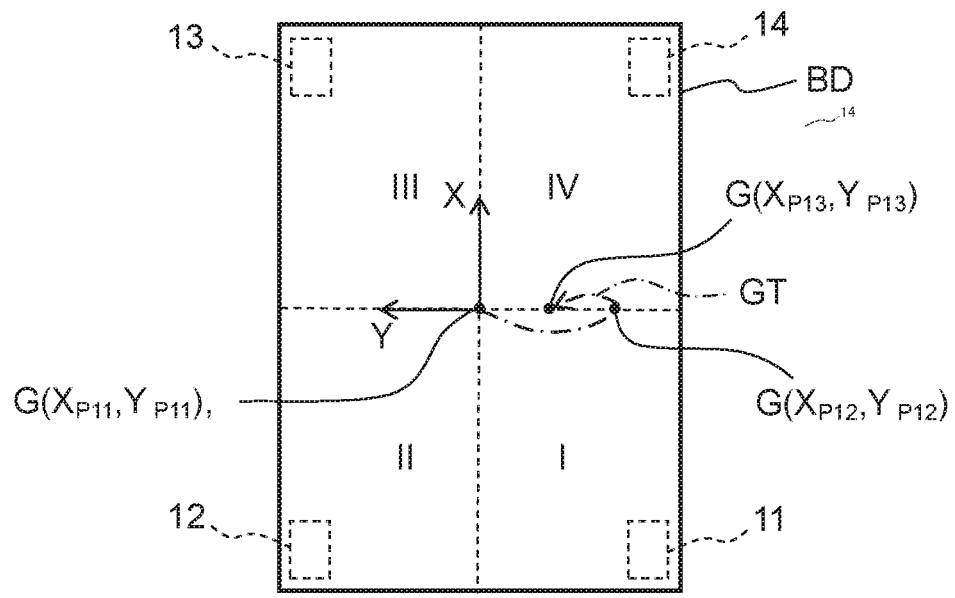
FIG. 6 depicts exemplary locus of the center of gravity of a subject.

In the center of gravity locus calculating step S02, the center of gravity position calculation unit 33 calculates the position G (X, Y) of the center of gravity G of the subject S on the bed BD at a predetermined period T (for example, a period equal to the sampling period of 5 milliseconds described above) on the basis of the load signals $s_1$ to $s_4$ fed from the load detectors 11 to 14 to acquire (obtain) the temporal variation of the position of the center of gravity G of the subject S (center of gravity locus GT). In this case, (X, Y) indicates the coordinates on the XY coordinate plane in which X extends in the longitudinal direction of the bed BD and Y extends in the lateral direction of the bed BD while the central portion of the bed BD is the origin (FIG. 6).

The calculation of the position G (X, Y) of the center of gravity G by the center of gravity position calculation unit 33 is performed in accordance with the following operation. That is, G (X, Y) is calculated in accordance with the following expressions assuming that the coordinates of the load detectors 11, 12, 13, 14 are $(X_{11}, Y_{11})$, $(X_{12}, Y_{12})$, $(X_{13}, Y_{13})$, and $(X_{14}, Y_{14})$ respectively, and the detection values of the load detectors 11, 12, 13, 14 are $W_{11}$, $W_{12}$, $W_{13}$, and $W_{14}$ respectively.

$$X = \frac{X_{11} \times W_{11} + X_{12} \times W_{12} + X_{13} \times W_{13} + X_{14} \times W_{14}}{W_{11} + W_{12} + W_{13} + W_{14}}$$ (Numerical expression 1)

$$Y = \frac{Y_{11} \times W_{11} + Y_{12} \times W_{12} + Y_{13} \times W_{13} + Y_{14} \times W_{14}}{W_{11} + W_{12} + W_{13} + W_{14}}$$ (Numerical expression 2)

The center of gravity position calculation unit 33 acquires the temporal variation of the position G (X, Y) of the center of gravity G, i.e., the center of gravity locus GT while calculating the position G (X, Y) of the center of gravity G at the predetermined sampling period T on the basis of the numerical expressions (1) and (2) described above. The acquired center of gravity locus GT is stored, for example, in the storage unit 4.

An example of the center of gravity locus GT calculated by the center of gravity position calculation unit 33 is depicted in FIG. 6. FIG. 6 depicts the positions G ($X_{P11}$, $Y_{P1}$), G ($X_{P12}$, $Y_{P12}$), G ($X_{P13}$, $Y_{P13}$) of the center of gravity G of the subject S on the bed BD at the time $t_{110}$, $t_{120}$, $t_{130}$ included in the periods $P_{11}$, $P_{12}$, $P_{13}$ depicted in FIG. 5 respectively. An arrow of alternate long and short dash line to connect these positions indicates the center of gravity locus GT of the center of gravity G of the subject S moving from the position G ($X_{P11}$, $Y_{P11}$) to G ($X_{P13}$, $Y_{P13}$).

In this embodiment, the biological information analysis unit 34 analyzes the presence or absence of a body motion of the subject S and the manner of a body motion of the subject S on the basis of the center of gravity locus GT of the subject S calculated as above by the center of gravity position calculation unit 33. Specifically, for example, the biological information analysis unit 34 calculates the movement speed (movement amount per unit time) of the center of gravity G on the basis of the changes in the position of the center of gravity G of the subject S at the respective points in time, stored in the storage unit 4, and when the calculated speed exceeds a predetermined threshold, the biological information analysis unit 34 determines that the subject S has performed a body motion. Note that a body motion of the subject S includes a body motion caused by a relatively large movement of the body involving the movement of the body portion (body trunk) of the subject S (large body motion), such as turning over, and a body motion caused by a relatively small movement of the body not involving the movement of the body portion of the subject S (small body motion), such as movement of hands, feet, and/or face. A large body motion is, specifically, turning over, sitting up or the like. When a large body motion occurs to the subject, the direction of the body axis of the subject (the direction in which the backbone of the subject extends) changes in general. A small body motion is, specifically, for example, the movement only of hands, feet, and/or head.

When the large body motion is defined in view of the manner of the temporal variation of the position of the center of gravity, the large body motion can be defined in general to be the movement of the center of gravity for a relatively long distance exceeding a predetermined distance, which occurs within a predetermined time period. Alternatively, it is also possible to define, on the basis of the difference from the temporal variation of the position of the center of gravity caused by the small body motion, for example, that the large body motion is the body motion in which the center of gravity is moved, within a predetermined time period, at least nearly predetermined times as greatly as the movement distance of the center of gravity by the small body motion. Further, it is also allowable to define, by comparing with the amplitude of the respiratory oscillation as described later on.

When the small body motion is defined in view of the manner of the temporal variation of the position of the center of gravity, the small body motion can be defined in general to be the movement of the center of gravity for a relatively short distance within a predetermined time period. Further, it is also allowable to define, by comparing with the amplitude of the respiratory oscillation as described later on. Further, it is also allowable to define that the small body motion is the body motion to cause the movement of the center of gravity for a relatively short distance within a predetermined time period, the movement of the center of gravity not being an oscillation in a constant direction. According to this definition, when an attention is paid to the movement of the center of gravity, it is possible to further clearly distinguish the small body motion from the respiration.

Here, in the center of gravity locus calculating step S02, as depicted in the numerical expressions (1) and (2) described above, the center of gravity position G (X, Y) is calculated on the basis of the entire loads $W_{11}$, $W_{12}$, $W_{13}$, and $W_{14}$ detected by the load detectors 11, 12, 13, 14 respectively. Accordingly, for example, when any object is placed in a position away from the subject S on the bed, the center of gravity position G (X, Y) calculated by the numerical expressions (1) and (2) described above may be displaced (deviated) from the actual center of gravity position of the subject 5, by the influence of the load of the object which has been placed on the bed. For this reason, in this embodiment, the components included in a specified frequency range (band) are separated from each of the load signals $s_1$ to $s_4$ outputted from the load detectors 11 to 14 to also calculate the center of gravity position of the subject S on the basis of the separated components.

Figure 7:
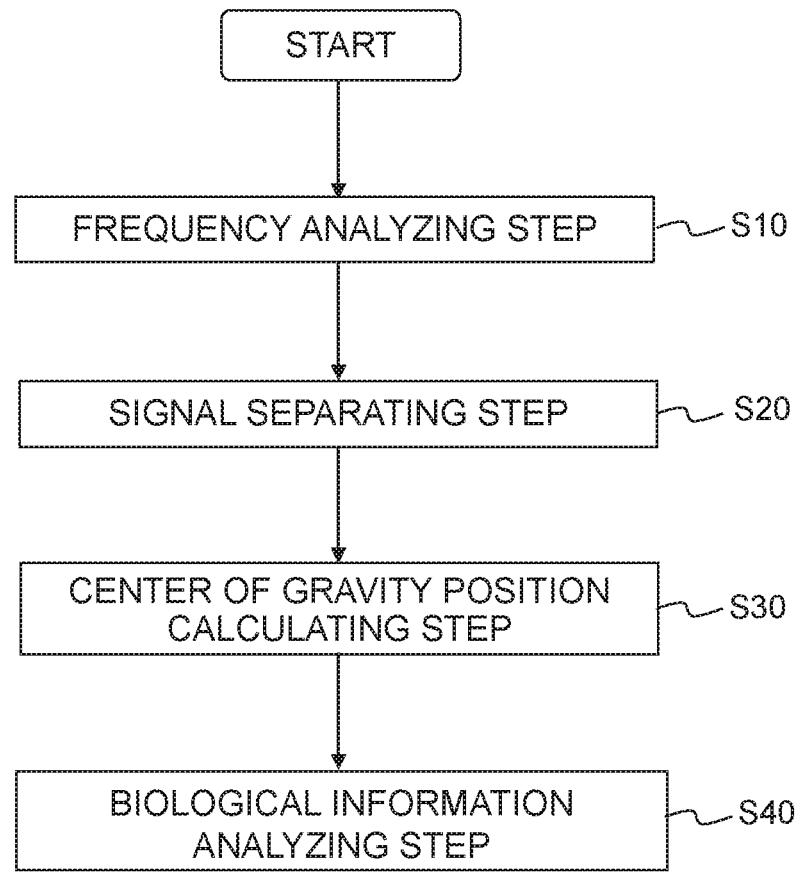
FIG. 7 is a flow chart depicting a method for calculating the center of gravity position of a subject on the basis of the respiration component or the heartbeat component which has been separated from each load signal.

In the following, with reference to the flow chart in FIG. 7, an explanation will be given about the process of separating the components included in the frequency range of respiration (about 0.2 Hz to about 0.33 Hz) from each of the load signals $s_1$ to $s_4$, and calculating the center of gravity position of the subject S on the basis of the separated components.

In a frequency analyzing step S10, the frequency analysis unit 31 acquires a frequency spectrum by performing the Fourier transformation of each or at least one of the load signals $s_1$ to $s_4$ outputted from the load detectors 11 to 14.

In a signal separating step S20, the signal separation unit 32 specifies a peak frequency included in the frequency range of respiration (i.e., frequency of the respiration of the subject S) based on the frequency spectrum acquired in the frequency analyzing step S10. Then, the signal separation unit 32 separates components $s_{b1}$ to $s_{b4}$ (hereinafter referred to as "respiration components"), corresponding to the specified peak frequency, from the load signals $s_1$ to $s_4$ respectively.

In a center of gravity position calculating step S30, the center of gravity position calculation unit 33 calculates the center of gravity position $G_b$ (X, Y) of the subject S on the bed in accordance with the numerical expressions (1) and (2) described above, on the basis of the respiration components $s_{b1}$ to $s_{b4}$ separated in the signal separating step 20.

In a biological information analyzing step S40, the biological information analysis unit 34 may adopt either of the center of gravity position G (X, Y) calculated on the basis of the entire loads and the center of gravity position $G_b$ (X, Y) (respiratory center of gravity, center of gravity of respiration) calculated on the basis of the respiration components $s_{b1}$ to $s_{b4}$. For example, after comparison of the center of gravity position G (X, Y) calculated on the basis of the entire loads with the center of gravity position $G_b$ (X, Y) calculated on the basis of the respiration components $s_{b1}$ to $s_{b4}$, the biological information analysis unit 34 may determine which to adopt as the center of gravity position of the subject S. Alternatively, the distance between the center of gravity position G (X, Y) based on the entire loads and the center of gravity position $G_b$ (X, Y) based on the respiration components is calculated, and when the calculated distance exceeds a predetermined range, the biological information analysis unit 34 may adopt the center of gravity position $G_b$ (X, Y) based on the respiration components as the center of gravity position of the subject S. In this case, the predetermined range may be appropriately set in consideration of, for example, the dimension(s) of the bed, the body height and weight of the subject S, and the like.

The biological information analysis unit 34 analyzes various biological information of the subject S by using the adopted center of gravity position.

By the way, the respiration of human is performed by moving the chest and the diaphragm to expand and shrink the lungs. In this context, when the air is inhaled, i.e., when the lungs are expanded, the diaphragm is lowered downwardly, and the internal organs are also moved downwardly. On the other hand, when the air is expired, i.e., when the lungs are shrunk, the diaphragm is raised upwardly, and the internal organs are also moved upwardly. As a result of the research performed by the inventors of the present disclosure, it has been found out that in accordance with the movement of the internal organs, the center of gravity G oscillates approximately along the extending direction of the backbone (body axis direction) (hereinafter referred to as "respiratory oscillation").

Therefore, when the center of gravity position is subject to the respiratory oscillation in a specified direction, the biological information analysis unit 34 regards the specified direction as the direction of the body axis of the subject S, and determines the posture of the subject S on the bed (whether the body axis is parallel to the longitudinal direction of the bed or inclined with respect to the longitudinal direction of the bed). The direction of the respiratory oscillation can be specified, for example, by specifying a certain extreme point (extreme value point) and an extreme point appearing immediately before or immediately after the certain extreme point from the locus of the respiration oscillation, and acquiring the axis connecting both of the extreme points.

Further, the biological information analysis unit 34 draws a respiratory waveform of the subject S with a longitudinal axis as a direction of the body axis and a lateral axis as a time axis, by plotting distances, each between the center of oscillation of the respiratory oscillation and the position obtained by projecting the center of gravity position at each point in time to the body axis. Then, the biological information analysis unit 34 counts the number of maximum values or minimum values appearing on the respiratory waveform to thereby determine the respiration rate of the subject S. Furthermore, based on the amplitude of the center of gravity position (i.e., amplitude of the respiratory oscillation, or amplitude of the respiratory waveform), the biological information analysis unit 34 calculates a respiratory ventilation volume (tidal volume) per one respiration of the subject S (depth of the respiration).

Next, with reference to the flow chart in FIG. 7, an explanation will be given about the process of separating the components included in the frequency range of heartbeat (about 0.5 Hz to about 3.3 Hz; hereinafter referred to as "heartbeat range") from each of the load signals $s_1$ to $s_4$, and calculating the center of gravity position of the subject S on the basis of the separated components. Note that this process may be carried out in parallel to the calculation of the center of gravity position $G_b$ (X, Y) based on the respiration components described above, or may be solely carried out.

In the frequency analyzing step S10, the frequency analysis unit 31 acquires a frequency spectrum in the heartbeat range, by performing the Fourier transformation of each or at least one of the load signals $s_1$ to $s_4$ outputted from the load detectors 11 to 14.

In the signal separating step S20, the signal separation unit 32 specifies a peak frequency included in the heartbeat range (i.e., frequency of the heartbeat of the subject S) based on the frequency spectrum acquired in the frequency analyzing step S10. Then, the signal separation unit 32 separates the components $s_{h1}$ to $s_{h4}$ (hereinafter referred to as "heartbeat components"), corresponding to the specified peak frequency, from each of the load signals $s_1$ to $s_4$.

In the center of gravity position calculating step S30, the center of gravity position calculation unit 33 calculates the center of gravity G of the subject S on the bed in accordance with the numerical expressions (1) and (2) described above, on the basis of the heartbeat components $s_{h1}$ to $s_{h4}$ separated in the signal separating step 20 (hereinafter such center of gravity G referred to as "center of gravity $G_h$ based on the heartbeat components (heartbeat center of gravity, center of gravity of heartbeat)").

The center of gravity $G_h$ based on the heartbeat components of the subject S on the bed as calculated by using the heartbeat components $s_{h1}$ to $s_{h4}$ separated from the load signals $s_1$ to $s_4$ have the following characteristics.

(1) The center of gravity $G_h$ based on the heartbeat components is calculated by using only the heartbeat components $s_{h1}$ to $s_{h4}$, among the load signals $s_1$ to $s_4$, which oscillate corresponding to the heartbeat of the subject S. Consequently, for example, in the case that a load by a third party (such as a visitor) whose heartbeat has a frequency different from that of the heartbeat of the subject S, or a load by an inanimate object (such as a bag) having no heartbeat is added on the bed BD, the center of gravity $G_h$ based on the heartbeat components remains unmoved, and the center of gravity $G_h$ based on the heartbeat components moves only in the case that the subject S has moved.

(2) As a result of the observation, by the inventors of the present disclosure, of the locus of movement of the center of gravity $G_h$ based on the heartbeat components, it has been found out that the center of gravity $G_h$ based on the heartbeat components slightly oscillates along the direction obtained by rotating the body axis of the subject S counterclockwise to some degree. This oscillation (hereinafter referred to as "heartbeat oscillation") is considered to be caused by the beating of the heart.

In the biological information analyzing step S40, the biological information analysis unit 34 may compare the center of gravity position G (X, Y) calculated on the basis of the entire loads with the position of the center of gravity $G_h$ based on the heartbeat components, and determine which to adopt as the center of gravity position of the subject S. This determination can be made in accordance with the method same as or equivalent to the method explained above concerning the center of gravity position $G_b$ (X, Y) based on the respiration components.

Further, the biological information analysis unit 34 can also determine whether or not the subject S exists on the bed BD, namely, make a presence-on-bed determination, on the basis of whether or not it is possible to acquire the center of gravity $G_h$ based on the heartbeat components. When the subject S does not exist on the bed BD, the components, which vary according to the heartbeat of the subject S, do not exist in each of the load signals $s_1$ to $s_4$ of the load detectors 11 to 14. Consequently, it is not possible to separate such components, and it is not possible to calculate the center of gravity $G_h$ based on the heartbeat components. For this reason, the presence-on-bed determination can be made on the basis of the presence or absence of the heartbeat components or whether or not it is possible to calculate the center of gravity $G_h$ based on the heartbeat components. The biological information analysis unit 34 may determine that the subject S exists on the bed, for example, when it is confirmed that the calculated center of gravity $G_h$ based on the heartbeat components exists on the bed BD. More precisely, when it is confirmed that the center of gravity $G_h$ based on the heartbeat components is oscillating in a predetermined direction which is inclined with respect to the body axis of the subject S, the biological information analysis unit 34 may determine that the subject S exists on the bed.

Furthermore, the biological information analysis unit 34 can acquire the direction of the body axis of the subject S, on the basis of the direction of oscillation of the center of gravity $G_h$ based on the heartbeat components, and can also acquire a heart rate, on the basis of the oscillation rate per one minute of the center of gravity $G_h$ based on the heartbeat components.

The effects of the biological information monitoring system 100 of this embodiment are summarized as follows.

The signal separation unit 32 of this embodiment separates, for example, the respiration components included in the frequency range of respiration and the heartbeat components included in the frequency range of heartbeat, from each of the load signals $s_1$ to $s_4$ outputted from the load detectors 11 to 14. Then, the center of gravity position calculation unit 33 of this embodiment calculates not only the center of gravity position G (X, Y) calculated on the basis of the entire loads, but also the center of gravity position $G_b$ (X, Y) based on the respiration components and the center of gravity position $G_h$ (X, Y) based on the heartbeat components. Consequently, the biological information analysis unit 34 can utilize the center of gravity position $G_b$ (X, Y) based on the respiration components and the center of gravity position $G_h$ (X, Y) based on the heartbeat components for analyzing various biological information of the subject S. The center of gravity position $G_b$ (X, Y) based on the respiration components and the center of gravity position $G_h$ (X, Y) based on the heartbeat components remain unchanged when a load not deriving from the subject S, such as a load of baggage or a visitor, is added on the bed BD, so that using these center of gravity positions makes it possible to further accurately analyze biological information of the subject S.

For example, by using the center of gravity position $G_b$ (X, Y) based on the respiration components, the biological information analysis unit 34 can analyze the posture (body axis direction) of the subject S on the bed and the respiratory condition such as respiratory waveform (respiration waveform), respiratory rate (respiration rate), and respiratory ventilation volume.

Further, based on the presence or absence of the heartbeat components or the center of gravity $G_h$ based on the heartbeat components, the biological information analysis unit 34 can make a presence-on-bed determination with respect to the subject S. Unlike the respiration, the heartbeat cannot be stopped consciously (deliberately, intentionally), and thus, present (exist, settling) on/leaving (absent) from the bed of the subject S can be further reliably determined, by making a presence-on-bed determination on the basis of the presence or absence of the heartbeat components or the center of gravity $G_h$ based on the heartbeat components.

The biological information monitoring system 100 of this embodiment acquires biological information of the subject S by using the load detectors 11 to 14 arranged under the legs of the bed BD. Therefore, it is unnecessary to attach any measuring device to the body of the subject S. Neither discomfort nor sense of incongruity is given to the subject S.

Modified Embodiment

In the biological information monitoring system 100 of the embodiment described above, the following modified embodiment may be adopted.

For example, the respiratory cycle (cycle of the respiration) differs depending on the sex (gender), physique (physical constitution), lung capacity and the like of a subject S, and the heartbeat cycle (cycle of the heartbeat) also differs from person to person. Consequently, when a plurality of subjects S exist on the bed BD, different peak frequencies as many as the number of the subjects S appear in the frequency range of respiration and/or the frequency range of heartbeat in the frequency spectrum acquired in the frequency analyzing step S10.

In view of the above, when a plurality of peak frequencies appear in the frequency range of respiration and/or the frequency range of heartbeat, the signal separation unit 32 may determine that a plurality number of subjects S are on the bed, and separate the respiration components and/or the heartbeat components corresponding to each of the subjects S, from each of the load signals $s_1$ to $s_4$. Then, the center of gravity position calculation unit 33 may calculate the center of gravity position of each of the subjects S on the basis of the respiration components and/or the heartbeat components corresponding to each of the subjects S. For example, when a peak appears in each of a frequency $v_1$ and a frequency $v_2$ in the frequency range of respiration, the signal separation unit 32 determines that two subjects S are on the bed. In the signal separating step S20, the signal separation unit 32 separates the respiration components corresponding to the frequency $v_1$ and the respiration components corresponding to the frequency $v_2$, from each of the load signals $s_1$ to $s_4$. Then, in the center of gravity position calculating step S30, the center of gravity position calculation unit 33 calculates the center of gravity position $G_{b1}$ (X, Y) based on the respiration components corresponding to the peak frequency $v_1$ and the center of gravity position $G_{b2}$ (X, Y) based on the respiration components corresponding to the peak frequency $v_2$.

According to the modified embodiment described above, even when a plurality number of subjects S are on the bed, it is possible to separately acquire the center of gravity $G_b$ based on the respiration of each of the subjects S and the center of gravity $G_h$ based on the heartbeat of each of the subjects S, and the center of gravity position of each of the subjects S can be accurately grasped.

In the biological information monitoring system 100 of the embodiment described above, the biological information analysis unit 34 may determine that the subject S has settled on the bed, when the load added to the bed BD increases by at least a predetermined value (for example, about 40 kg) and the heat beat components or the center of gravity $G_h$ based on the heartbeat have/has been acquired. The biological information analysis unit 34 may determine that the subject S has left the bed, when the load added to the bed BD decreases by at least a predetermined value and the heat beat components or the center of gravity $G_h$ based on the heartbeat are/is unable to be acquired.

Note that when there exists on the bed BD an element striking the bed BD with a predetermined period or cycle (impact element), waveform having such predetermined period or cycle appears in each of the load signals $s_1$ to $s_4$ fed from the load detectors 11 to 14, four waveforms in the load signals $s_1$ to $s_4$ having phases identical to each other. If a load component including such waveform is separated by using the frequency analysis unit 31 and the signal separation unit 32, and the separated load component is used for the center of gravity position calculation unit 33 to calculate a center of gravity position, it is possible to calculate the center of gravity position of the impact element.

In the embodiment described above, each of the load detectors 11, 12, 13, 14 is not limited to the load sensor having the beam-type load cell. It is also possible to use, for example, a force sensor.

In the embodiment described above, the number of load detectors is not limited to four. It is also allowable to use five or more load detectors by providing an additional leg or additional legs for the bed BD. Alternatively, it is also allowable to arrange the load detectors for only three of the legs of the bed BD. Even when the three load detectors are used, it is possible to detect a position of the center of gravity G of the subject S on the plane of the bed BD provided that the three load detectors are not arranged on a straight line.

Figure 8:
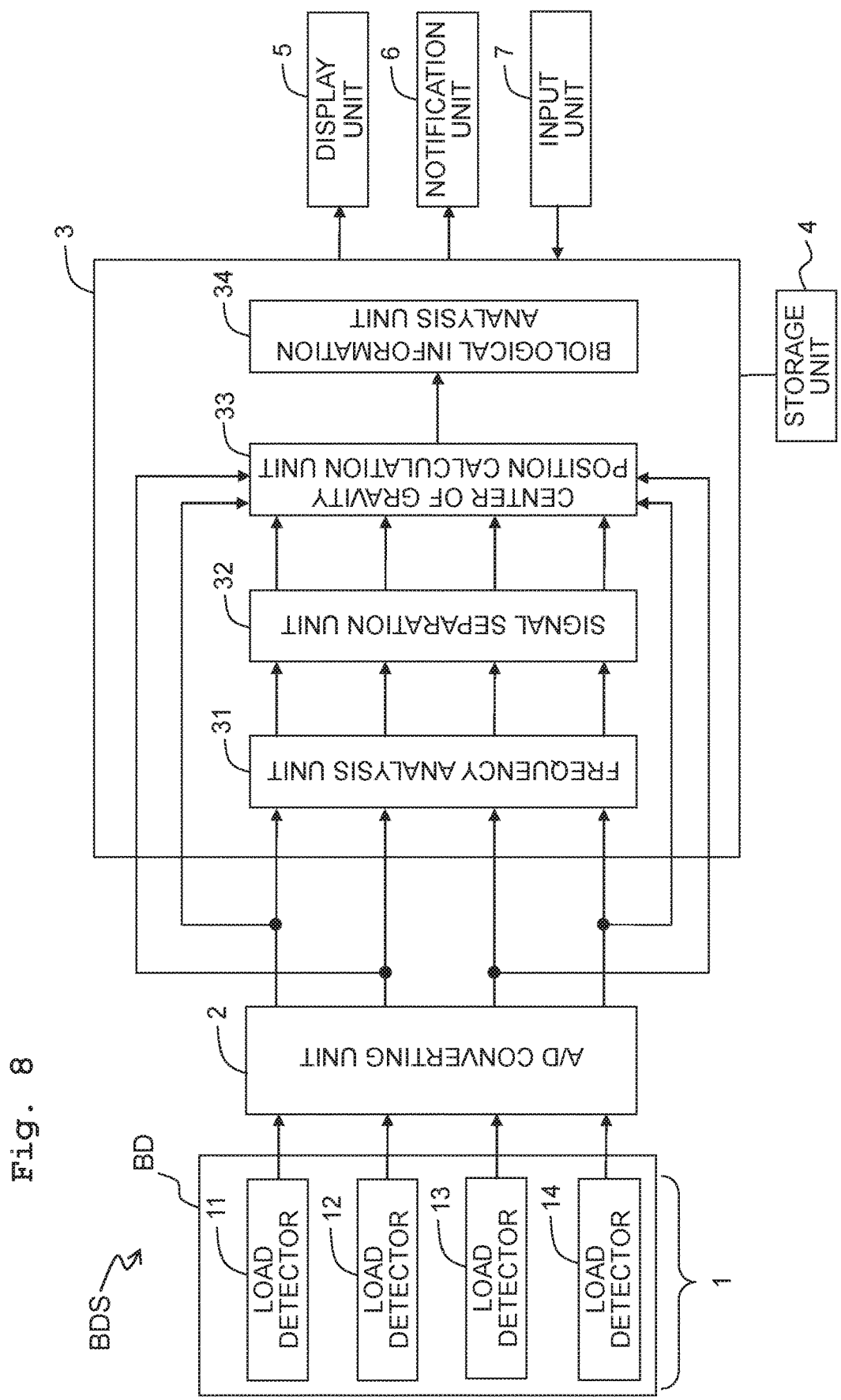
FIG. 8 is a block diagram depicting an entire configuration of a bed system according to a modified embodiment.

In the embodiment described above, the load detectors 11, 12, 13, 14 are arranged respectively on the undersides of the casters $C_1$, $C_2$, $C_3$, $C_4$ attached to the lower ends of the legs of the bed BD. However, there is no limitation thereto. Each of the load detectors 11, 12, 13, 14 may be provided respectively between each of the four legs of the bed BD and the board of the bed BD. Alternatively, if each of the four legs of the bed BD can be divided into upper and lower portions, each of the load detectors 11, 12, 13, 14 may be provided between upper leg and lower leg. Further alternatively, the load detectors 11, 12, 13, 14 may be formed integrally with the bed BD to construct a bed system BDS comprising the bed BD and the biological information monitoring system 100 of this embodiment (FIG. 8). Note that in this specification, the "load detectors placed in the bed" means the load detectors each of which is provided between one of the four legs of the bed BD and the board of the bed BD as described above and the load detectors each of which is provided between the upper leg and the lower leg.

In the embodiment described above, it is also allowable to provide a signal amplifying unit for amplifying the load signal fed from the load detecting unit 1 and/or a filtering unit for removing the noise from the load signal, between the load detecting unit 1 and the A/D converting unit 2.

In the biological information monitoring system 100 of the embodiment described above, the display unit 5 is not limited to the unit which displays the information on the monitor so that the user can make the visual recognition. For example, the display unit 5 may be a printer which periodically prints and outputs the respiratory condition (respiratory rate, respiratory ventilation volume), the state of the heartbeat, and the physical condition of the subject S. Alternatively, the display unit 5 may be a unit which performs the display by using any simple visual expression, for example, such that a blue lamp is turned ON in the case of the presence-on-bed state and/or a red lamp is turned ON in the case of the bed-leaving state. Further alternatively, the display unit 5 may be a unit which reports the biological information of the subject S to the user by means of any sound or voice. Further alternatively, it is also allowable that the biological information monitoring system 100 does not have the display unit 5. The biological information monitoring system 100 may have only an output terminal for outputting the information. A monitor (display device) or the like, which is provided to perform the display, will be connected to the biological information monitoring system 100 by the aid of the output terminal.

The notification unit 6 of the embodiment described above performs the notification auditorily. However, the notification unit 6 may be constructed to perform the notification visually by means of, for example, the flashing or flickering of light. Alternatively, the notification unit 6 may be constructed to perform the notification by means of the vibration. Further, it is also allowable that the biological information monitoring system 100 of the embodiment described above does not have the notification unit 6.

The present invention is not limited to the embodiments described above provided that the feature of the present invention is maintained. Other embodiments, which are conceivable within the scope of the technical concept of the present invention, are also included in the scope of the present invention.

The biological information monitoring system according to the above embodiments may further include a presence-on-bed determination unit configured to determine that the subject exists on the bed, based on the load component which oscillates according to the heartbeat of the subject.

In the biological information monitoring system according to the above embodiments, the presence-on-bed determination unit may be configured to determine that the subject has settled on the bed, based on the load component which oscillates according to the heartbeat of the subject and an increase, beyond a predetermined value, of a load applied onto the bed.

In the biological information monitoring system according to the above embodiments, the load separation unit may be configured such that, in a case that the subject is a plurality of subjects on the bed, the load separation unit separates the load of the subject into a plurality of loads each corresponding to each of the plurality of subjects based on a frequency spectrum of a temporal variation of the load of the subject detected by at least one of the plurality of load detectors, and separates a load component which oscillates according to a heartbeat of each of the plurality of subjects from each of the plurality of loads of the plurality of subjects, and the center of gravity position calculation unit may be configured to obtain a position of a center of gravity of each of the plurality of subjects based on the load component which oscillates according to the heartbeat of each of the plurality of subjects.

In the biological information monitoring system according to the above embodiments, the load separation unit may be further configured to separate a load component which oscillates according to a respiration of the subject, from the load by the subject, and the center of gravity position calculation unit may be further configured to obtain a position of a respiratory center of gravity of the subject based on the load component which oscillates according to the respiration of the subject.

In the biological information monitoring system according to the above embodiments, the load separation unit may be configured such that, in a case that the subject is a plurality of subjects on the bed, the load separation unit separates the load of the subject into a plurality of loads each corresponding to each of the plurality of subjects based on a frequency spectrum of a temporal variation of the load of the subject detected by at least one of the plurality of load detectors, and separates a load component which oscillates according to a heartbeat of each of the plurality of subjects and a load component which oscillates according to a respiration of each of the plurality of subjects, from each of the plurality of loads of the plurality of subjects, and the center of gravity position calculation unit may be configured to obtain a position of a heartbeat center of gravity of each of the plurality of subjects based on the load component which oscillates according to the heartbeat of each of the plurality of subjects, and obtain a position of a respiratory center of gravity of each of the plurality of subjects based on the load component which oscillates according to the respiration of each of the plurality of subjects.

According to the biological information monitoring system of an aspect of the present disclosure, it is possible to grasp a center of gravity position of the subject on the bed accurately.

The invention claimed is:

1. A biological information monitoring system for monitoring a biological information on a subject on a bed, the system comprising:
   a plurality of load detectors which are to be placed in the bed or under legs of the bed, and which are configured to detect loads of the subject, respectively; and
   a controller configured to control the biological information monitoring system, wherein the controller is configured to control the biological information monitoring system to:
   calculate a frequency spectrum of a temporal variation of at least one of the loads of the subject detected by the plurality of load detectors, so as to separate load components, each of which oscillates according to a heartbeat of the subject, from the loads of the subject, respectively, based on the frequency spectrum;
   obtain a position of a center of gravity of the subject, at each sampling time, based on the separated load components, each of which oscillates according to the heartbeat of the subject, and obtain a locus of the obtained center of gravity oscillating according to the heartbeat of the subject; and
   determine and display that the subject exists on the bed, based on at least one of the load components, each of which oscillates according to the heartbeat of the subject.

2. The biological information monitoring system according to claim 1, wherein the controller is configured to determine and display that the subject has settled on the bed, based on at least one of the separated load components, each of which oscillates according to the heartbeat of the subject and an increase, beyond a predetermined value, of a load applied onto the bed.

3. The biological information monitoring system according to claim 1, wherein:
   the controller is configured such that, in a case that the subject is a plurality of subjects on the bed, the controller separates each of the loads of the subject into a plurality of loads each corresponding to each of the plurality of subjects based on the frequency spectrum of the temporal variation of the load of the subject detected by at least one of the plurality of load detectors, and separates a load component which oscillates according to a heartbeat of each of the plurality of subjects from each of the plurality of loads of the plurality of subjects, and
   the controller is configured to obtain a position of a center of gravity of each of the plurality of subjects, at each sampling time, based on the separated load component which oscillates according to the heartbeat of each of the plurality of subjects so as to obtain for each of the plurality of subjects the locus of the center of gravity oscillating according to the heartbeat of the subject.

4. The biological information monitoring system according to claim 1, wherein:
   the controller is further configured to separate a load component which oscillates according to a respiration of the subject, from the loads of the subject, based on the frequency spectrum, and
   the controller is further configured to obtain a position of a respiratory center of gravity of the subject, at each sampling time, based on the separated load component which oscillates according to the respiration of the subject so as to obtain a locus of the respiratory center of gravity oscillating according to the respiration of the subject.

5. The biological information monitoring system according to claim 4, wherein:
   the controller is configured such that, in a case that the subject is a plurality of subjects on the bed, the controller separates each of the loads of the subject into a plurality of loads each corresponding to each of the plurality of subjects based on the frequency spectrum of the temporal variation of the load of the subject detected by at least one of the plurality of load detectors, and separates a load component which oscillates according to a heartbeat of each of the plurality of subjects and a load component which oscillates according to a respiration of each of the plurality of subjects, from each of the plurality of loads of the plurality of subjects, and
   the controller is configured to obtain a position of a heartbeat center of gravity of each of the plurality of subjects, at each sampling time, based on the separated load component which oscillates according to the heartbeat of each of the plurality of subjects so as to obtain for each of the plurality of subjects a locus of the heartbeat center of gravity oscillating according to the heartbeat of the subject, and obtain a position of a respiratory center of gravity of each of the plurality of subjects, at each sampling time, based on the separated load component which oscillates according to the respiration of each of the plurality of subjects so as to obtain for each of the plurality of subjects a locus of the respiratory center of gravity oscillating according to the respiration of the subject.

6. The biological information monitoring system according to claim 1, wherein the controller is configured to determine and display that the subject exists on the bed when the controller determines that the center of gravity of the subject exists on the bed.

7. The biological information monitoring system according to claim 1, wherein the controller is configured to:
   obtain a direction of a body axis of the subject based on a respiratory oscillation, of a center of gravity based on the load of the subject, according to a respiration of the subject, and
   draw a respiratory waveform of the subject by plotting distances each between a center of the respiratory oscillation and a position obtained by projecting the center of gravity based on the load of the subject at each sampling time to the body axis of the subject.

* * * * *